United States Patent [19]

Gravenstein et al.

[11] Patent Number: 5,560,351

[45] Date of Patent: Oct. 1, 1996

[54] TRANSTRACHEAL ENERGY APPLICATION AND SENSING SYSTEM FOR INTUBATION: METHOD AND APPARATUS

[75] Inventors: Dietrich Gravenstein, Salt Lake City, Utah; Nikolaus Gravenstein, Gainesville, Fla.; Richard J. Melker, Gainesville, Fla.; Samsun Lampotang, Gainesville, Fla.; Anwer Sultan, Gainesville, Fla.

[73] Assignee: University of Florida, Gainesville, Fla.

[21] Appl. No.: 319,543

[22] Filed: Oct. 7, 1994

[51] Int. Cl.$^6$ ................................................. A61M 16/04
[52] U.S. Cl. ........................ 128/200.26; 128/205.23; 128/207.14; 128/207.15
[58] Field of Search ................. 128/200.26, 205.23, 128/207.14, 207.15

[56] References Cited

U.S. PATENT DOCUMENTS

| | | | |
|---|---|---|---|
| 4,063,561 | 12/1977 | McKenna | 128/207.15 |
| 4,244,362 | 1/1981 | Anderson | 128/207.14 |
| 4,567,882 | 2/1986 | Heller | 600/120 |
| 4,943,770 | 7/1990 | Ashley-Rollmen et al. | 128/737 |
| 5,125,406 | 6/1992 | Goldstone et al. | 128/733 |
| 5,257,636 | 11/1993 | White | 128/897 |
| 5,445,144 | 8/1995 | Wodicka et al. | 128/207.14 |

*Primary Examiner*—Aaron J. Lewis
*Attorney, Agent, or Firm*—Kerkam, Stowell, Kondracki & Clarke; Dennis P. Clarke

[57] ABSTRACT

An intubation scope assembly adapted to facilitate the positioning of an endotracheal tube in a patient comprising an electromagnetic or sound energy source which enters the vocal cords exteriorly of the neck of the patient with energy having a direction, wavelength and intensity capable of entering the trachea, substantially avoiding encompassing the entire pharynx and capable of being transmitted cephalad substantially between and/or around the vocal cords. A suitable sensor for the energy emitted by such source comprises a stylet assembly, the distal end of which can detect or collect the energy transmitted between and/or around the vocal cords and the proximal end of which can monitor the detected or collected energy to thereby locate the vocal cords for positioning an endotracheal tube therebetween. A system and method of intubating a patient with the foregoing assembly are also disclosed.

16 Claims, 4 Drawing Sheets

5,560,351

TRANSTRACHEAL ENERGY APPLICATION AND SENSING SYSTEM FOR INTUBATION: METHOD AND APPARATUS

BACKGROUND OF THE INVENTION

1. Field of the Invention

The present invention relates to intubation devices and, more particularly, to a device and method for inserting and confirming the placement of an endotracheal tube (ETT) in the trachea of a patient.

2. Description of the Prior Art

Certain types of illnesses and clinical conditions and injury can cause a patient's airway to become blocked or otherwise impaired, preventing adequate oxygenation and ventilation of the patient. When this occurs, prompt corrective action must be taken. Oftentimes, this action requires the placement of an ETT in the patient's trachea in order to restore or maintain an adequate airway. The process of inserting the tube in the patient is commonly referred to as intubation.

Over the years, various types of intubation devices have been developed for inserting endotracheal tubes in a patient. Perhaps the most commonly used intubation technique is a process known as direct laryngoscopy. In this technique, a device called a laryngoscope is used to actually visualize the upper airway through the patient's mouth during the process of inserting the ETT. This technique is usually successful in ensuring correct placement of the tube in the trachea in most patients. However, direct laryngoscopy is not feasible under all circumstances. Indeed, performing intubation on a relaxed, well-prepared patient in a hospital setting is much different than attempting to intubate an accident victim in a moving ambulance, helicopter or at the scene. Moreover, direct laryngoscopy has the disadvantage of increasing the risk of hypertension, tachycardia and dental and soft tissue trauma.

When intubation is properly performed, regardless of the procedure employed, the inserted end of the endotracheal tube will be positioned in the patient's trachea at a location substantially between the patient's vocal cords and carina. This location has been found to provide the best and most reliable airway management for several reasons. If the tube is not inserted far enough past the vocal cords, for example, it can become dislodged and ineffective, such as when it ends up in the esophagus. If the tube is inserted too far into the trachea, however, past the carina, then the tube may only function to adequately ventilate one of the lungs, rather than both. This can lead to serious complications. Thus, proper placement of the inserted end of the tube plays a major role in the intubation process.

Various techniques have been used in the past to attempt to ensure that the ETT lies in the proper location between the patient's vocal cords and carina after intubation. One such technique involves placing a light at the inserted end of the ETT prior to intubation. The technique is based on the principle of transillumination, i.e., that a strong light can be transmitted through the cartilage and soft tissues of the neck. It was further discovered that when the light at the end of the tube was clearly visible through the patient's skin in the area of the sternal notch, then the inserted end of the tube was approximately half-way between the vocal cords and carina in most patients. The absence of a clear glow of illumination in this area usually indicates incorrect placement, such as in the esophagus.

Even the most skilled and experienced laryngoscopist may encounter what is termed a "difficult" airway, which may occur in as many as 5% of all intubations. Difficult airways are identified several ways. A patient may report an extremely sore throat or nose after a previous surgery or there may be documentation on a previous anesthetic record. The jaw, teeth, mouth opening and neck motion are always examined prior to intubation to help gauge the difficulty of laryngoscopy. These maneuvers can identify many, but not all, difficult airways. In the traumatized patient, concern over a potentially unstable cervical spine that if manipulated, as is customary during laryngoscopy, could lead to paralysis is also considered a difficult airway. Of course, there is always the difficult airway that is discovered at the time of intubation despite no physical examination findings or surgical history to suggest its presence (unusual anatomy, undetected masses in the airway, etc.).

How the difficult airway is approached depends very much on the skill of the care giver and the circumstances necessitating an ETT for the patient. Currently, a number of techniques are commonly employed. These include traditional laryngoscopy with or without axial cervical traction, fiber-optic bronchoscopy with or without a transtracheal retrograde wire guide, blind nasal and the lighted stylet techniques. Certain situations may preclude use of any of these methods and require emergent cricothyrotomy or tracheostomy.

The fiber-optic bronchoscopic technique is considered to be the method of choice in elective situations because it allows visualization of the vocal chords and trachea to confirm correct ETT placement. The major drawbacks with the fiberscope are (1) that it requires substantial expertise and (2) its poor performance in patients with copious secretions or blood in their airway. Thus, the patient is usually administered an anti-sialogogue to decrease secretions and a topical vasoconstrictor to reduce bleeding caused from the trauma that can be associated with oral and nasal intubations. Because blood so easily compromises the fiberscopic view and renders the fiberscope useless, it is often impractical and unnecessarily time-consuming to attempt this method of intubation in the traumatized victim. Although advances have been made in miniaturization of the fiberscope, the smaller-diameter fiberscopes that will pass through the smallest diameter ETTs are prohibitively expensive. Further drawbacks to the fiberscope are that it requires an external power supply for its light source, it is a large instrument and occupies substantial space at the patient's head, as well as for storage. All fiberscopes are expensive and sensitive instruments which are easily broken.

In selected patients, it may be preferable to employ the retrograde wire technique. This method requires that a needle be placed through the anterior neck into the trachea. A wire is passed through the needle and is then advanced upward through the vocal cords and pharynx until it emerges from the nose or mouth. The wire acts as a guide for either an ETT alone or a fiberscope loaded with an ETT. This method identifies the most prominent anatomical structure in the neck, namely, the trachea, and establishes a path for the ETT or fiberscope to follow in order to properly place the ETT there. One drawback to this technique is that it is invasive and risks introducing bleeding and infection into the trachea. Another drawback is that the wire must be stiff enough to act as a guide for the ETT alone. A stiff wire is more prone to injure tissues such as the trachea and vocal cords when advanced cephalad than would a more flexible wire. If the wire can act only as a visual guide for the fiberscope, then this method is also disadvantaged in bloody or secretion-abundant environments.

The lighted stylet is a device that incorporates aspects of both the fiberscope and retrograde wire techniques. In design, it is simply a stylet with a bright light at the distal end and a battery power source at the other end. An ETT is loaded over the stylet such that the light just emerges from the distal end of the ETT. When properly placed in the mouth, the light from the stylet will shine between the vocal cords into the trachea and the operator will see a pretracheal glow on the external neck. Once this glow is identified, the ETT is advanced and proper ETT placement reconfirmed through customary means [Birmingham et al, *Anesth. Analg.*, Vol. 65, pp. 886–891 (1986)]. Thus, the lighted stylet is like the fiberscope in that it uses a light source in the airway and that the stylet acts as a platform from which to place the ETT. It is like the retrograde wire in that an observation or event occurs on the neck, namely, the pretracheal glow, that confirms correct positioning of the stylet. The lighted stylet overcomes many of the disadvantages of the fiberscope and retrograde wire techniques. Unlike the fiberscope, the lighted stylet is small, easily stored, rugged, does not require an extra power source, is disposable, relatively inexpensive and works well in a bloody environment. Unlike the retrograde wire technique, it does not risk additional infection or bleeding, and acts as its own ETT placement platform.

The lighted stylet method, however, is fraught with difficulties. Because it relies on the operator to appreciate a pre-tracheal glow before advancing the ETT, it is best used in a dark environment on thin and lightly pigmented patients. In fact, the lighted stylet is extremely difficult to use even by experienced operators in controlled situations if the patient has a large neck, is darkly pigmented or there is much ambient light. Unfortunately, visualization of the pretracheal glow may require the medical attendant to leave his customary position at the head of the patient and stand beside the patient. Intubation from this position is not necessarily more difficult, but it does significantly compromise the caregiver's ability to divert vomitus away from the airway if the patient regurgitates, and/or to stabilize the head and neck should the patient begin to move.

Furthermore, because of the light bulb that is at the tip of the stylet, its greatest outer diameter can only be reduced a small amount. Therefore, the lighted stylet will not easily pass through smaller-diameter ETTs. Children under the age of approximately 6 years would be too small to benefit from a lighted stylet. These pitfalls are commonly encountered by emergency rescue teams in the field, as well as in the emergency and operating rooms. Thus, the lighted stylet fails to achieve desirable design objectives of being a reliable intubation adjunct for all difficult airways because it can be used with confidence only with selected patients in selected situations.

A new method for securing the airway is needed. This method should be reliable under all conditions where emergent airway or difficult airways may be encountered. It must work equally well in bright light and in the dark. It must be lightweight, small, portable, durable and inexpensive. It must be able to function properly in all sizes of patients, in patients with light or heavy pigmentation and in situations where there is blood in the airway. Finally, it must not require an excessive amount of experience to use the device with effectiveness and safety.

It is an object of the present invention to provide an intubation system and method which satisfies these criteria and overcomes the disadvantages associated with the prior art devices.

SUMMARY OF THE INVENTION

The above and other objects are realized by the present invention, one embodiment of which provides an intubation scope assembly adapted to facilitate the positioning of an endotracheal tube in the trachea of a patient comprising an electromagnetic or sound energy source and a suitable sensor for the energy emitted by such source.

The energy source comprises means for directing or passing electromagnetic or sound energy between and/or around the vocal cords from the exterior of the neck of the patient, the energy having a direction, wavelength and intensity to reach the trachea, substantially avoid encompassing the entire pharynx and capable of being transmitted cephalad substantially between and/or around the vocal cords.

The energy sensor comprises a stylet assembly. In one embodiment of the stylet assembly, the distal end has mounted thereon means to detect the energy transmitted between and/or around the vocal cords by the above-described energy source and the proximal end contains means for monitoring the detected energy to thereby locate the vocal cords for positioning an endotracheal tube therethrough. In a second embodiment, the stylet functions as an energy guide (light guide, fiber-optic guide, sound guide or the like), the distal end comprising energy collecting means which transmit the energy from the above-described source by internal reflection or conduction to the proximal end of the stylet which contains or communicates with means to detect and monitor the energy.

A second embodiment of the invention relates to a method of intubating a patient with an endotracheal tube having a distal end for insertion into the patient's trachea and a proximal end outside the patient, the improvement comprising passing electromagnetic or sound energy substantially between and/or around the vocal cords of the patient, the energy being transmitted externally of the neck, the energy having a direction, wavelength and intensity to enter the trachea, to substantially avoid encompassing the entire pharynx and to be transmitted cephalad substantially through and/or around the vocal cords; sensing the energy transmitted through and/or around and thereby locating the vocal cords of the patient and routing the distal end of the endotracheal tube between the located vocal cords and correctly placing the same in the trachea.

A further embodiment of the invention relates to a system comprising an endotracheal tube adapted for the intubation of a patient: (1) mounted around the above-described intubation scope assembly, the latter being removable from the endotracheal tube after placement in the trachea, or (2) containing within a wall thereof at least a portion of the above-described intubation scope assembly.

DETAILED DESCRIPTION OF THE INVENTION

Figure 1:
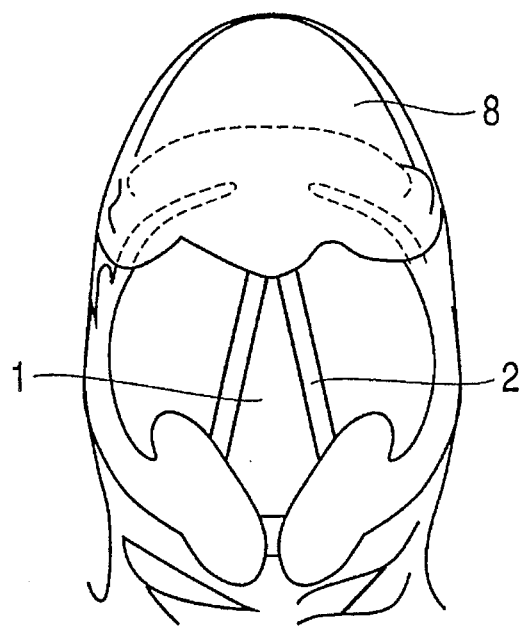
FIG. 1 depicts a view of a human larynx, the "cap" of the trachea, as seen during laryngoscopy.
Figure 2:
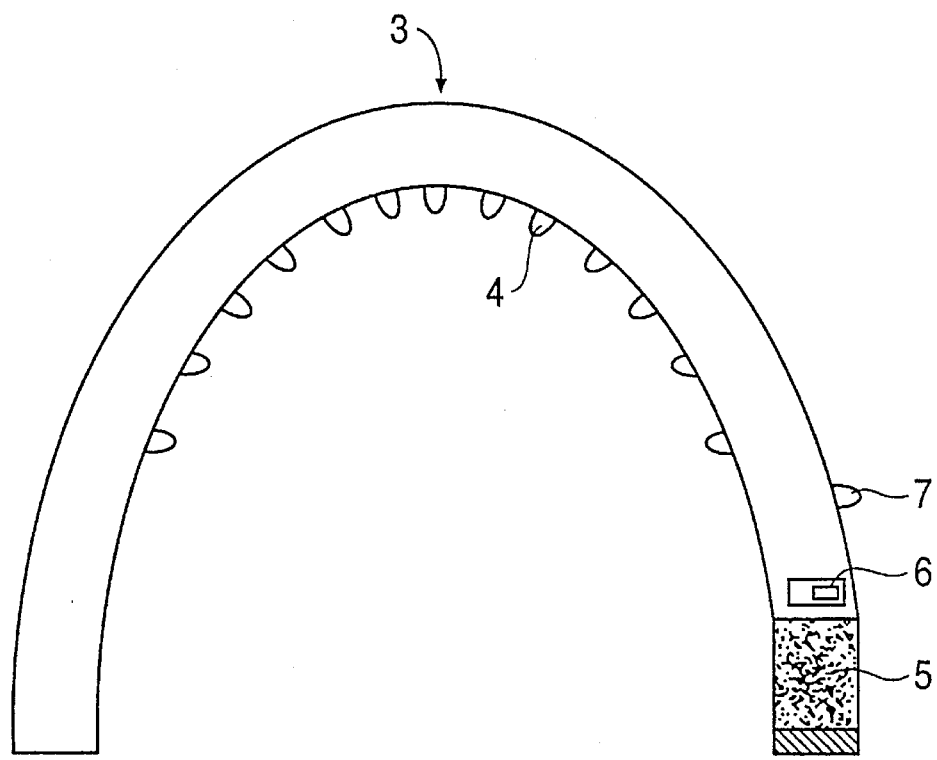
FIG. 2 is an elevational view of one embodiment of a transtracheal light illumination system according to the invention.

Referring to FIGS. 1 and 2, the present invention is predicated on the discovery that the application of, e.g., a light energy source emitting light of a specific critical wavelength and intensity to the anterior neck results in the illumination of the trachea (1) such that the light travels cephalad and shines like a beacon between the vocal cords (2). The trachea is an easily located and palpable structure in the anterior neck. Light sensors, mounted for example on a stylet, are utilized to detect the light emanating from between the vocal cords (2) and enable the operator of the system to advance the ETT into its proper location, i.e., between the vocal cords (2) and into the trachea (1).

When employing sound energy which, unlike electromagnetic energy, is much better conducted through fluid-conducting structures such as tissues than air, the operator of the system would be "listening" for a sound "hole" which would coincide with the tracheal column of air. This is, of course, opposite of an electromagnetic energy based system which conducts light much better through air than tissue and would have the operator of the system "looking" for a maximal light intensity coming from between the vocal cords.

Principal design considerations for the light source apparatus applied to the neck of the patient are the apparatus shape, the optimal light wavelength and intensity to be emitted. It is preferable that the light source can be applied to the neck and will not require an assistant to hold the same in place as a single operator intubation system is envisioned. It is also preferable that no strap be used to hold the light source on the patient's neck as placement of a strap around the neck may cause undesired cervical motion, compromise blood flow to and from the patient's head, make spontaneous breathing more difficult and may be otherwise distressing to the patient. Use of a double-sided adhesive strip to apply the light source may work well in most cases, but may be problematic in a patient whose neck may be wet from sweat, rain and/or blood. A C-shaped light source (3) that is slipped onto the neck and fixes the light source orientation with respect to the neck meets all of these desired design objectives without obvious cases where failure is probable. Light emitting diodes (LED) (4) or broad band fiber-optic light sources can be used as the light source in such an assembly to uniformly and reliably illuminate the trachea, even if deviated or situated deeper within the neck than normal. LEDs offer an inexpensive method of emitting a specific wavelength of light at high intensity. Laser diodes are more expensive, but have narrower peak bandwidths and deliver a higher intensity light than the LEDs. These attributes may be desirable in some situations. A third alternative is to use a high intensity white light source and shine it through an infrared filter to eliminate unwanted radiation in those wavelengths most associated with tissue heating. This may offer the least expensive method for generating a bright, wavelength-specific light source for the illumination of the trachea. Any of these light sources can be directly applied to the neck or utilize a fiber-optic cable to transmit light to the desired location. A self-contained apparatus would require a battery pack (5), on-off switch (6) and battery test-lamp (7).

In the illustrative case of employing electromagnetic energy, e.g., light, the selection of light wavelength is perhaps the most crucial aspect of the invention. The wavelength chosen should be rapidly absorbed or scattered by soft tissues and water. Such a characteristic of the signal light would avoid undesired illumination of the entire pharynx. Thus, only light transmitted between or through the thin vocal cords (1) would be detected, all other light having been substantially absorbed by the soft tissues of the neck and larynx (8). It is important to note that such a wavelength need not necessarily be in the visible spectrum since it is not mandatory that it be seen by the human eye as it will be detected by sensors. However, if a tissue is illuminated continuously, this light wavelength and intensity must not cause thermal or other injury to the tissues illuminated thereby. Because the use of fiber-optic fibers in the final design is anticipated, the light should be of suitable wavelength to be conducted through such fibers.

Generally, electromagnetic radiation having a wavelength between about 550 nm and about 5,500 nm may be utilized in the practice of the invention. The intensity of the incident radiation will depend on the wavelength thereof and the sensitivity of the detector. The energy transmission through tissues is strongly influenced by the wavelength of the incident energy. Wavelengths above about 600 nm penetrate tissues up to 10,000 times better than shorter wavelengths due to less reflection and absorption and more forward scattering of the radiant energy. However, water absorbs energy more efficiently as wavelengths increase above 1,300 nm setting the practical upper limit wavelength in the region stated. Those practiced in the art of electromagnetic/sound detection must ultimately define the intensity and frequency of incident radiation/sound energy necessary for reliable detection after transillumination. As sensor technology continues to improve, incident radiation and sound intensities required for reliable energy detection will be adjusted downward.

Figure 3:
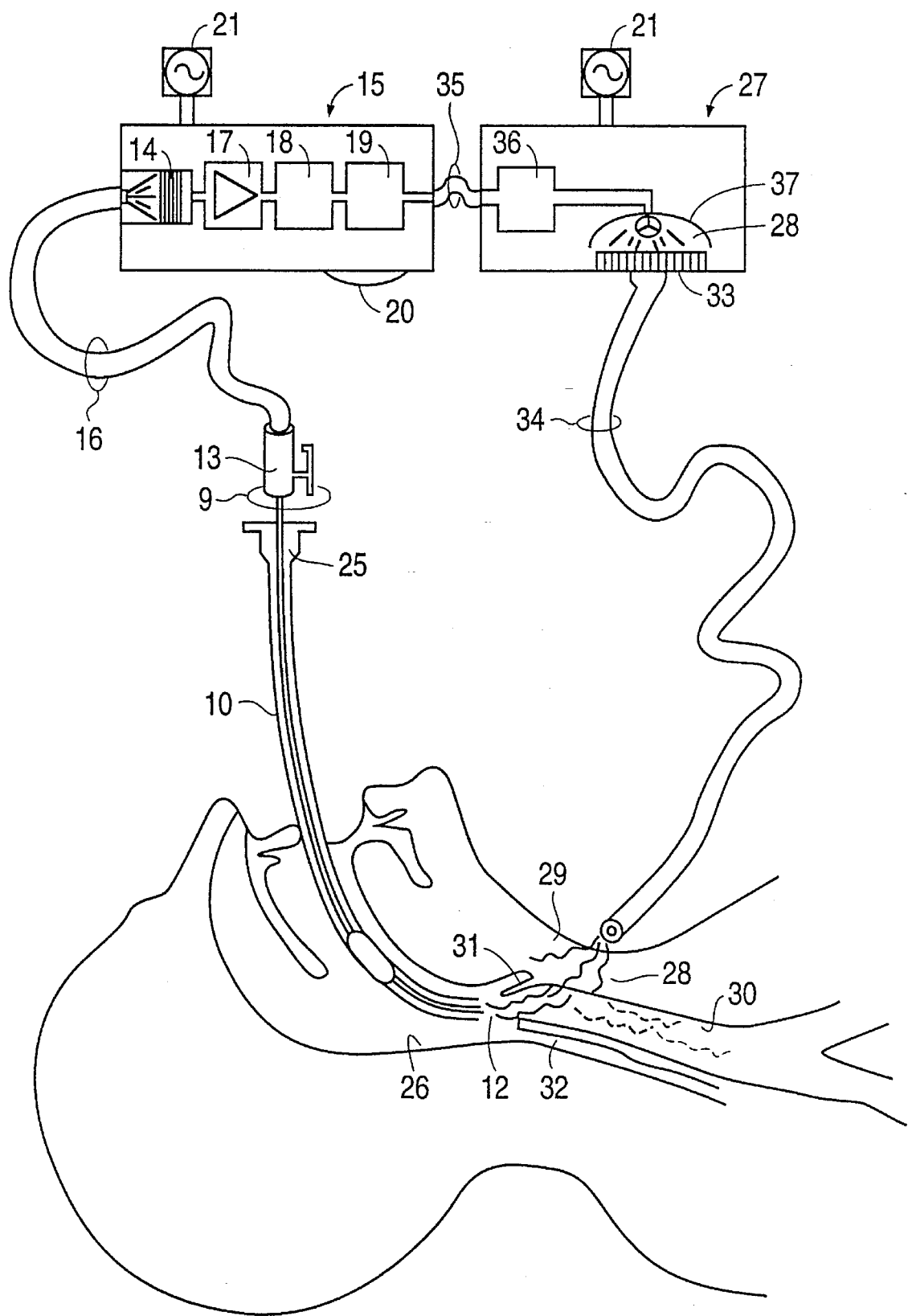
FIG. 3 depicts the components of a directionally sensitive energy sensing stylet and electronic circuit controlled light source as used for intubation of the trachea.

FIG. 3 shows the components crucial to the design of a hand-held movable stylet system (9) that will help direct it towards the light source. FIG. 3 depicts a disposable energy (light or sound) guide (10) contained in a malleable sleeve and stiffening element (11) (see FIGS. 4 and 5), a distal energy receiving end (12), and a connecting element (13) that attaches the energy guide (10) to an energy sensing element (14) located in a static element. This energy sensing element (14) may contain filters, amplifiers and lenses to optimize its performance. Also depicted is the static processing and steering system (15) which is attached to the movable stylet system (9) through a long connecting fiber-optic cable (16). Major components of the static system are a transimpedance amplifier (17) which increases the amplitude of the transduced signal, an analog-to-digital converter (18) which digitizes the analog signal before processing, contains a signal comparator for light source power optimization, electronic circuitry (19) which processes the digitized signal and contains the stylet steering algorithm, a tip-steering direction indicator (20) (as an audible indicator would be located on the static system, while a visual indicator would be situated on the movable stylet system), and a power source (21).

Figure 4:
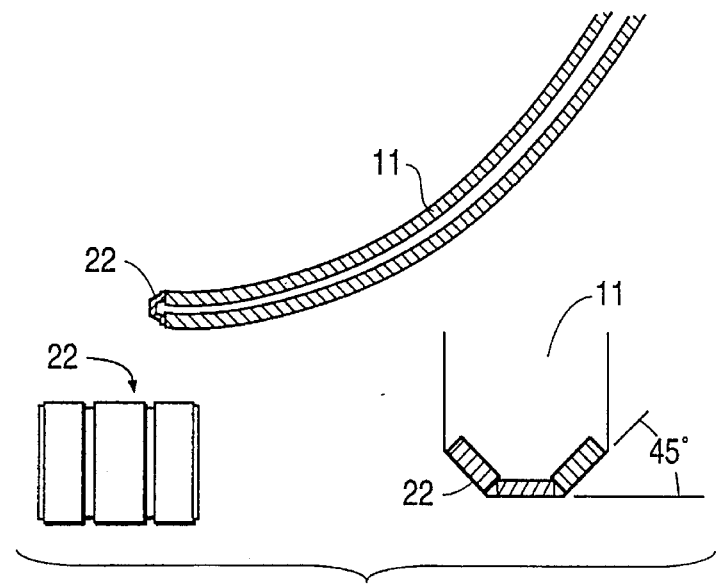
FIG. 4 represents several views of a sensing stylet embodiment of the invention.
Figure 5:
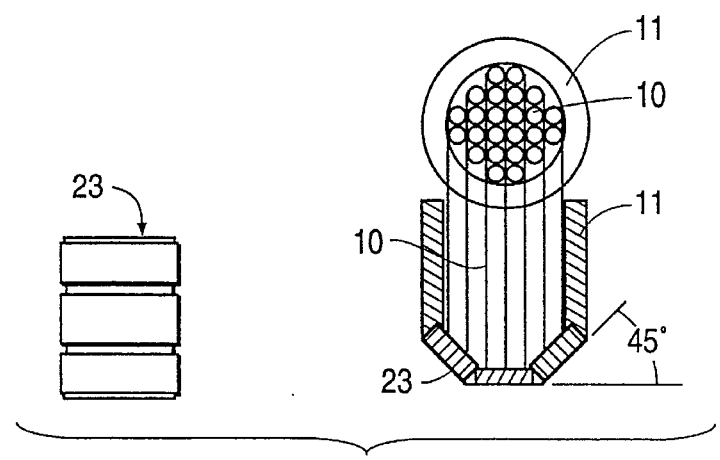
FIG. 5 represents a second embodiment of the sensing stylet and tip according to the invention.
Figure 6:
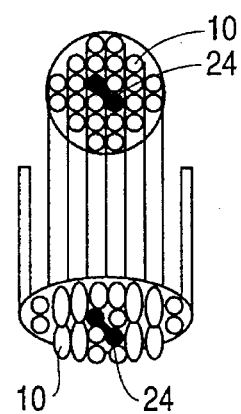
FIG. 6 is a third embodiment of a sensing stylet energy guide and tip according to the invention.

By applying detectors to the tip of a stylet (22), they can act as the "eye" to detect the light or other energy. FIG. 4 depicts several views of a stylet with energy detectors applied at the stylet tip. Use of detectors at the tip obviates the need for the stylet to also serve as an energy guide. Choosing the correct wavelength or signature, e.g., amplitude or frequency modulated, of light to emit and detect will make this device usable in all environments and immune to ambient light contamination. Dynamic orientation of the detector and emitter in relation to one another allows steering of the stylet between the vocal cords. Angled lenses (23) used with an energy guide (10), as depicted in several views in FIG. 5, are an alternate solution. FIG. 6 depicts a stylet with a malleable stiffening element (24) comprising its core. Around this stiffening element is the energy guide (10). As in FIG. 5, lenses could be applied to this configuration.

FIG. 3 depicts the present invention embodied in an endotracheal tube (25), the distal tip of which is placed in the hypopharynx (26) of a patient. An energy source (27) emits light (28) which is passed through an infrared filter (33) and conducted via a fiber-optic cable (34) to the neck (29) where it penetrates into the soft tissues and the trachea (30). The radiation transmitted through the soft tissues is rapidly scattered and absorbed. The radiation penetrating into the trachea travels partly in the cephalad direction, between the vocal cords (not shown) and past the epiglottis (31). The stylet tip is situated just anterior of the esophagus (32). Light (28) entering the energy guide (10) is transmitted via fiber-optic guides (10, 16) to the energy sensor (14) and to the static processing and steering system (15). This system, after processing the signals will indicate, either through audible or visual cues, in which direction the operator must advance the hand-held movable stylet system (9) to pass it towards the energy source or its conduit (34), between the vocal cords and into the trachea (30).

A preferred embodiment includes what is referred to in the description hereinbelow as a light intensity auto-gaining feature. What is accomplished by this feature is that the assembly will set the emitted light power to any level that is optimal for its performance in any given patient. This is a desirable feature because any given population of patients will have a variety of neck sizes and skin colors. These will range from the small, thin, pale baby's neck which has very little light absorption ability, to the large, thick and heavily pigmented laborer's neck. Obviously, using the best light power to transilluminate the airway of one of these subjects on the other would likely lead to failure.

To accomplish the autogaining feature, there is incorporated into the "static processing and steering system" a comparator integrated circuit (IC) chip. The function of this IC is to compare one input (in this case, the light intensity sensed from the stylet) against a second pre-programmed value. The pre-programmed value represents the optimal light intensity in the mouth that, when measured through the stylet system, produces an adequate signal by which an appropriate electronic circuit algorithm can steer the stylet into the trachea. If the comparator IC finds insufficient signal is detected, the electronic circuitry will increase the power output of the light source. Once the detected light power in the mouth is of adequate intensity, the power output of the light source is fixed and the homing/intubation sequence begins.

Figure 7:
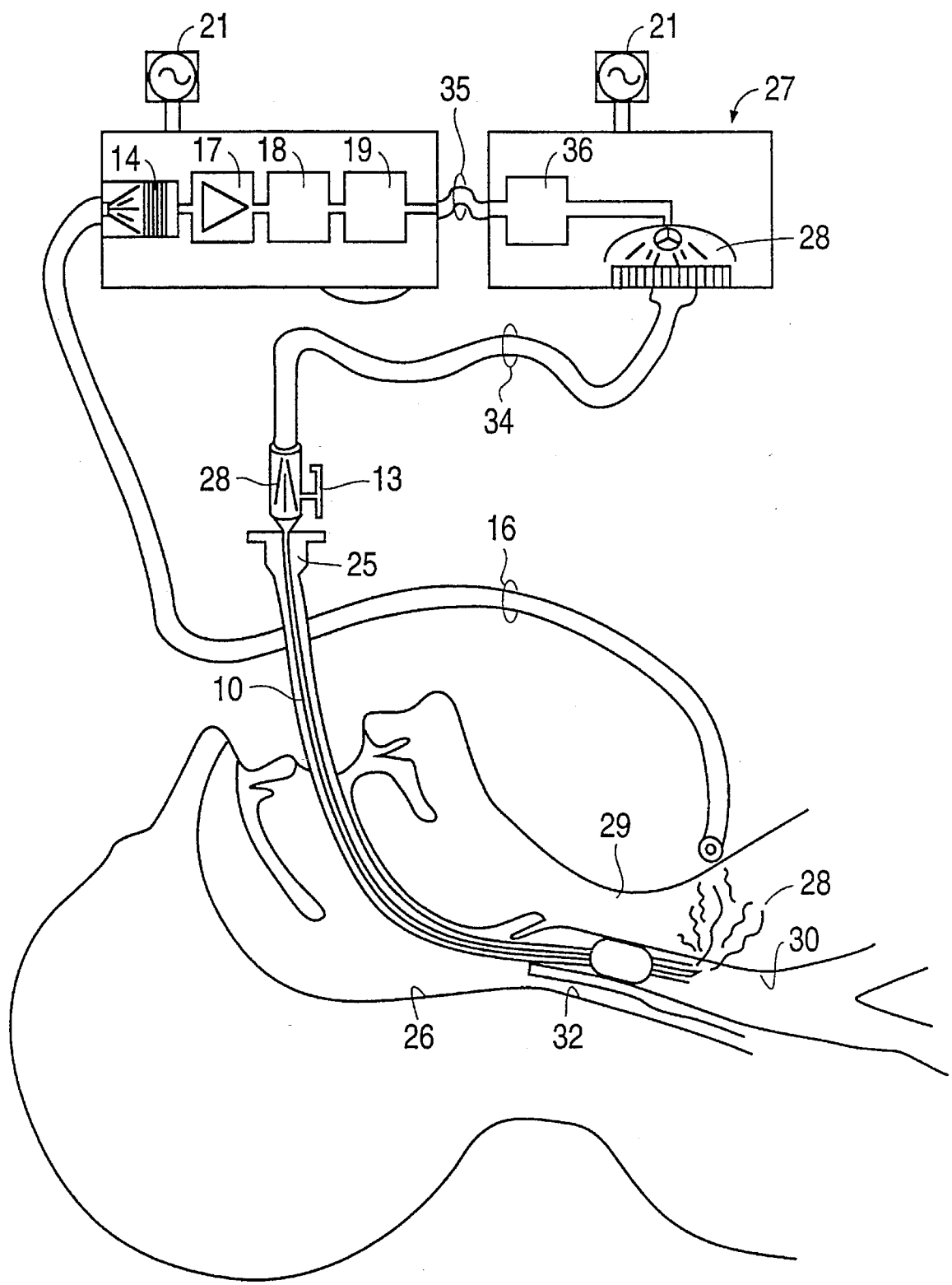
FIG. 7 depicts a cross-sectional view of an embodiment of the invention similar to that of FIG. 3 except that the application positions of the sensor and light source fiber-optic cables are reversed.

In order to influence light source power, the electronic circuitry and light source unit must be linked. Referring to FIGS. 3 and 7, a communication cable (35) connects the light source assembly (27) with the electronic circuit controller (19). A light source light intensity adjuster (36) (e.g., stepper motor, current controller) is positioned between the electronic circuitry and the light source (28). To actually effect a light power change, two features may be employed. The first feature incorporates a stepper motor that is actuated to turn a power intensity knob (similar to how room light dimming switches can be adjusted to dim or brighten a light by turning a knob). This solution is easily retrofitted onto commercially available light sources. The second feature comprises a current controller comprising appropriate electronic circuitry.

In a preferred embodiment, the light source element is a broad band light source assembly includes a reflecting dish and focusing element (37) that directs the light into the fiber-optic cable and an infrared light filter (33) which filters out the wavelengths (above 1,300 nm) known to cause heating of tissues.

The preferred embodiment is employed as follows: all equipment is powered on; the stylet ted endotracheal tube is placed into the mouth; the light source autogaining feature is activated and it quickly adjusts the light source intensity; when the autogaining sequence is completed, an auditory "chirp" is heard and the homing intubation begins.

It is understood by those skilled in the art that a number of energy sources and detectors can be used and that the location of the source and detector can be reversed such that the detector is on the neck and the energy source application is through the stylet apparatus.

Furthermore, it will be understood by those skilled in the art that any convenient energy (e.g., electromagnetic radiation, light, sound or the like) source (e.g., magnet, speaker, LED, laser or the like) may be utilized in the system and method of the invention provided that source emits energy of the appropriate wavelength and intensity to be detected by sensors (e.g., ammeter, photovoltaic cell or microphone) in the hypopharynx or, after having been conducted out of the patient via an energy guide, external to the patient.

It will be understood by those skilled in the art that the object of the method and apparatus of the invention is not simply to administer radiation to the pharynx or vocal cords. The object is to introduce a form of energy into (radiated energy) or around (sound energy) the airway. Detection of radiant energy in the pharynx that comes out of the trachea from between the vocal cords will be of high intensity because it will have been much less absorbed than the other radiant energy which is rapidly absorbed as it travels through tissues. Sound energy, which travels better in fluid than air media, when applied to the neck will, therefore, have its smallest intensity in the direction of the trachea and its greatest intensity in the direction of the soft tissues of the pharynx. Therefore, if sound is applied to the tissues of the external neck and a sound sensing device is used to locate the trachea, the device would "see" a sound 'hole' (little or no sound) in the direction of the air-filled trachea. Conversely, much more sound would be detected coming from the direction of the sound-conducting soft tissues. This is opposite of the way light or other radiant energy signals would be expected to work.

The preferred embodiment of the invention is illustrated in FIGS. 3 and 7. In this device, the stylet functions only as an energy guide (a light guide or fiber-optic guide in this case, although it could also be a sound guide) or conduit which transmits energy (light) with high efficiency by total internal reflection to the proximal end of the stylet, i.e., on the end that remains outside the patient as depicted in FIGS. 3 and 7, where an external photosensor (or other detector) transduces it into an electric signal and a steering algorithm processes it to provide audible or visible clues to the person operating the stylet. Thus, in this configuration, there are no photodetectors, although there may be lenses, at the distal tip of the stylet. The entire stylet is simply an energy guide (fiber-optic light guide). The distal tip will collect energy (light), possibly with the aid of small lens(es), and pass the light up the guide where sensor(s), which could be attached to the proximal end or be located more remotely, will detect it. This is a completely passive process until the sensor is reached. The illustration of this light guide (with lenses) is shown in FIG. 5. This simplicity of design enables the manufacture of the systems of the invention at low cost.

This configuration, with the light detection and monitoring system located at the proximal end of the stylet, allows the sensor or its energy conduit (e.g., fiber-optic cable) to be disconnected and placed on the neck and the light source or its energy conduit (e.g., a fiber-optic cable) that was on the neck to be attached to the proximal end of the stylet. This maneuver essentially switches the positions of the energy sensor and source. This maneuver is not possible if the sensor is on the distal end of the stylet deep inside the ETT and patient.

FIG. 7 depicts the reversed embodiment in an endotracheal tube (25), the distal tip of which is placed in the hypopharynx (26) of a patient. An energy source (27) emits light (28) through fiber-optic light guide (10), which light (28) penetrates into the soft tissues of the neck (29) and the trachea (30). The radiation transmitted through the soft tissues is rapidly scattered and absorbed. When the stylet tip is properly situated just anterior of the esophagus (32), light (28) emitted by the energy guide (10) is transmitted to the energy sensor (14) and to the static processing and steering system. The light source or a conduit (34) is attached to the ETT by means of a snap-on clip (13). Power is conveyed to the light source (27) via a power source (21). The distal end of the ETT is provided with a typical ETT cuff for positioning the distal end in the trachea. FIG. 7 depicts the light source attached to the fiber-optic stylet which, in this configuration, "pipes" light down the fiber-optic element at the distal end of the ETT where it emerges and is transmitted through the tissues of the pre-tracheal neck. As the light wavelength may not be in the visible spectrum, the photosensor (or its conduit) placed over the neck is expected to be used to precisely locate the endotracheal tube tip by identifying where the detected pre-tracheal light is most intense. However, it should be understood that the fiber-optic light guide need not necessarily be incorporated into the stylet used for intubation. This fiber-optic light guide could just as easily be an element incorporated into the wall of an endotracheal tube or a separate fiber-optic fiber which must be passed down the ETT lumen and is used expressly for the above-mentioned purposes. These alternative implementations may be more cost-effective methods for determining ETT position than the serial x-rays that are often required in patients who remain intubated for several days.

The illustration does not include a mechanism of how the photosensing element (or its conduit) is attached to a C-collar as this is but one way it could be used. More preferably, the photosensing element would be hand-held to allow the intubator to "roam" the neck and search for the area where the greatest light signal is being detected. This area then could coincide with the location of the underlying ETT's distal tip. One can also determine the position of the ETT tip (when illuminating the external neck and using the stylet as the sensor) by "roaming" with the light source until the frequency of the audible sound is greatest. At that point, the light source is right above the ETT tip. As for connecting the light source (or its conduit) to the light guide, there is illustrated a simple snap-on clip that could serve as such a connector. Other methods for introducing light into a fiber-optic conduit are well within the expertise of those practiced in the art of fiber-optic technologies.

Although this may appear similar to the lighted stylet of the prior art, the purpose for putting energy into the trachea is very different. Unlike the light stylet, it is not intended to use this arrangement to facilitate the placement of the endotracheal tube into the trachea. Placement of the ETT is to be accomplished via energy being applied to the external neck with a stylet-mounted sensor (sensor on the proximal or distal end of the stylet) used to steer the ETT loaded stylet between the vocal cords and into the trachea. Once the ETT is in place, then the energy (light) source can be removed from the neck and applied to a light guide on the proximal (outside of patient) end of the ETT (a light guide stylet or other light guide element) and the sensor placed on the neck. This maneuver will confirm the position of the ETT in the trachea (or, if misplaced, in the esophagus), as well as define the depth of the ETT which can be gauged from how far the light guide is down the ETT and where the transmitted energy on the pre-tracheal neck is strongest. The lighted stylet of the prior art is a thick and rigid device that shines light principally in the forward direction which, in a patient, would be down the trachea into the lungs and is the reason the pre-tracheal glow from a lighted stylet is most frequently seen at the sternal notch (at the bottom of the neck and at the top of the sternum, where the chest starts). The device of the invention uses thin flexible fiber-optic light guides that can easily be made to shine from the trachea outward. By incorporating such a light guide into the body of an ETT or advancing such a fiber to the distal end of an ETT (the distance down the ETT to its distal end is easily determined since all ETTs have length measurements printed on their walls), introducing light (or other energy) and measuring the site of maximal light intensity on the pre-tracheal neck, one has with a simple test confirmed correctness and depth of ETT placement. Less importantly, the lighted stylet uses an incandescent light bulb at the tip of its stylet. The present invention uses an external energy (light) source and transmits that energy into and through the fiber-optic energy (light) guide using only the energy (light wavelengths) that optimally penetrates tissues, thereby reducing the total exposure to energy (radiation) of those tissues and making the system of the invention more sensitive. Additionally, the lighted stylet is limited to using light in the visible spectrum, whereas the present device, in either configuration, may be optimized to use only the light which performs best (including light that may be invisible to the human eye).

We claim:

1. An intubation scope assembly adapted to facilitate the positioning of an endotracheal tube in the trachea of a patient, comprising:

an electromagnetic or sound energy source, and a sensor for the electromagnetic or sound energy emitted by said source;

said electromagnetic or sound energy source comprising means for directing said energy between and/or around a patient's vocal cords from the exterior of a neck of a patient, the electromagnetic or sound energy having a direction, wavelength and intensity to reach a patient's trachea, substantially avoid encompassing a patient's entire pharynx and capable of being transmitted cephalad substantially between and/or around a patient's vocal cords;

said energy sensor comprising a stylet assembly having proximal and distal ends selected from the group consisting of:

(a) a stylet assembly, the distal end of which comprises means to detect said energy transmitted between and/or around a patient's vocal cords, means to transmit said detected energy to the proximal end thereof and the proximal end of which comprises means for monitoring said detected energy to thereby locate a patient's vocal cords for positioning therethrough an endotracheal tube, and (b) a stylet assembly, the distal end of which comprises means to collect said energy transmitted between and/or around a patient's vocal cords, means to transmit said collected energy to the proximal end thereof and the proximal end of which comprises means to detect and monitor said collected energy.

2. The intubation scope assembly of claim 1 wherein said energy source contains means for affixing said electromagnetic or sound energy source to the anterior neck.

3. The intubation scope assembly of claim 1 wherein said electromagnetic or sound energy source is light.

4. The intubation scope assembly of claim 1 wherein said electromagnetic or sound energy source comprises at least one light emitting diode.

5. The intubation scope assembly of claim 1 wherein said electromagnetic or sound energy source comprises at least one IR-filtered broad band white light source.

6. The intubation scope assembly of claim 1 wherein the wavelength of said electromagnetic or sound energy is such that it is rapidly absorbed or scattered by soft tissue and water, thereby substantially avoiding encompassing the entire pharynx.

7. The intubation scope assembly of claim 1 wherein said stylet is stylet assembly, the distal end of which comprises means to convert said detected energy into electric signals and the proximal end of which comprises means to process said electric signals into visible or audible cues to enable positioning of an endotracheal tube.

8. The intubation scope assembly of claim 1 wherein the means on said distal end of said stylet assembly for detecting said energy is at least one photodetector.

9. The intubation scope assembly of claim 1 wherein said distal end of said stylet assembly includes means for detecting said energy comprises plural energy sensors.

10. The intubation scope assembly of claim 9 wherein said plural energy sensors are mounted on said distal end of said stylet assembly so as to enable determination of the direction of transmittal of said energy through said vocal cords.

11. The intubation scope assembly of claim 10 wherein said proximal end of said stylet assembly contains means for monitoring said plural energy sensors so as to enable determination of the direction of transmittal of said energy between and/or around and thereby to locate the vocal cords.

12. The intubation scope assembly of claim 1 wherein said distal end of said stylet assembly for collecting said electromagnetic or sound energy comprises means for enhancing collection and transmittance of said electromagnetic or sound energy.

13. The intubation scope assembly of claim 12 wherein said means for enhancing collection and transmittance of said electromagnetic or sound energy is at least one lens.

14. The intubation scope assembly of claim 1 wherein said stylet is stylet assembly, the proximal end of which comprises means to detect said collected and transmitted energy and to convert said detected electromagnetic or sound energy into electric signals and means to process said electric signals into visible or audible cues to enable positioning of an endotracheal tube.

15. An endotracheal tube adapted for the intubation of a patient mounted around the intubation scope assembly of claim 1.

16. An endotracheal tube adapted for the intubation of a patient wherein at least a portion of the intubation scope assembly of claim 1 is contained within a wall of the endotracheal tube.

* * * * *